United States Patent [19]
Kilo et al.

[11] Patent Number: 5,692,657
[45] Date of Patent: Dec. 2, 1997

[54] STETHOSCOPE HOLDER

[76] Inventors: Katherine A. Kilo, 12518 Maret Dr., Sunset Hills, Mo. 63127; Charles J. Kilo, 9014 Stonebridge Dr., Richmond Heights, Mo. 63117

[21] Appl. No.: 642,057

[22] Filed: May 3, 1996

[51] Int. Cl.$^6$ ............................................. A45C 11/00
[52] U.S. Cl. ............................................. 224/269; 181/131
[58] Field of Search ............................................. 224/269, 678; 181/131

[56] References Cited

U.S. PATENT DOCUMENTS

| | | | |
|---|---|---|---|
| D. 303,146 | 8/1989 | Stamm | D24/134 |
| D. 345,274 | 3/1994 | Costa . | |
| D. 345,482 | 3/1994 | Costa . | |
| D. 375,161 | 10/1996 | Hart | D24/134 |
| 3,766,361 | 10/1973 | Swinyar et al. . | |
| 3,797,717 | 3/1974 | Collins | 224/231 |
| 5,171,087 | 12/1992 | Green . | |
| 5,451,725 | 9/1995 | Goldman | 181/131 |

*Primary Examiner*—Renee S. Luebke
*Attorney, Agent, or Firm*—Polster, Lieder, Woodruff & Lucchesi

[57] ABSTRACT

A stethoscope holder is provided which may be secured to a piece of apparel, such as a pocket of a lab coat or the waist band of a pair of pants. The stethoscope holder includes a base having a front surface and a back surface. A rib which is generally U-shaped in elevation and L-shaped in cross-section, extends out from the front surface of the base. The rib defines a generally U-shaped channel which removably receives either the bell or diaphragm section of the chest-piece. A notch is formed at a bottom of the curved section of the rib and is sized to accept the tubing of the stethoscope. A flexible finger extends from the front surface of the base, below the rib and offset from the center of the base, to hold at least one of the ear pieces of the stethoscope. A spring biased clip is hingedly mounted to the back surface of the base, near the top thereof and is operable to selectively and removably secure the holder to an item of apparel.

13 Claims, 1 Drawing Sheet

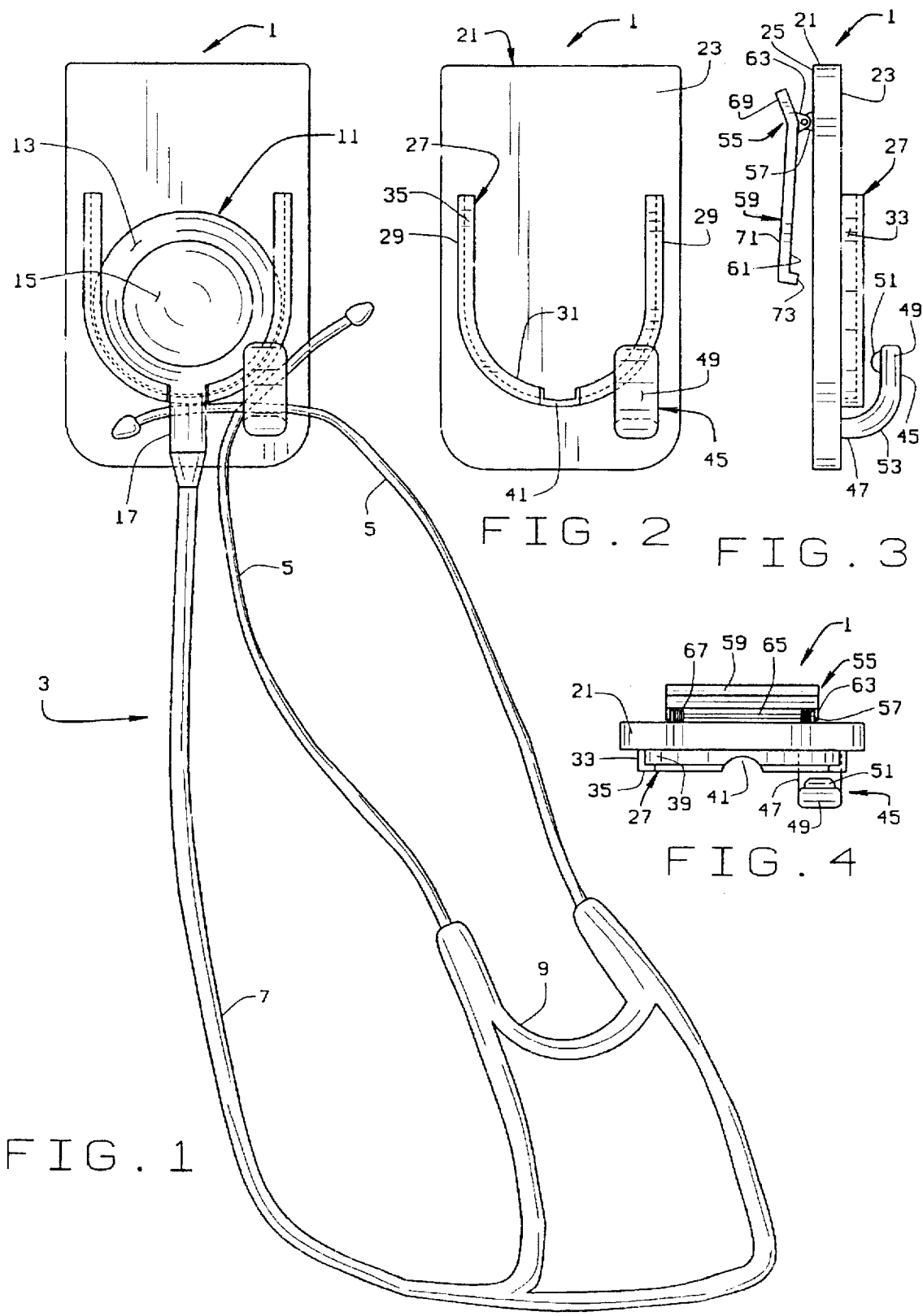

STETHOSCOPE HOLDER

BACKGROUND OF THE INVENTION

This invention relates to stethoscope holders, and in particular, a stethoscope holder which can be worn on clothing.

Health care professionals, such as doctors, nurses, and emergency medical personnel, etc. often carry a stethoscope with them. To carry the stethoscope, medical personnel either carry the stethoscope in the pocket of their lab coat or drape the stethoscope around their necks. In the first instance, the stethoscope is taking up room in the pocket of the lab coat which the health care professional may desire to use for other items, such as pens, pencils, vials, etc. Further, because the coat pocket is used to carry many different types of items, there may be debris in the pocket that is undesirable to get on a stethoscope. When a health care professional drapes the stethoscope around his/her neck, the stethoscope is not very stable, and may fall of when the health care professional bends over or rushes to an emergency.

SUMMARY OF THE INVENTION

One object of the present invention is to provide a stethoscope holder.

Another object is to provide such a stethoscope holder which is easy to use.

A further object is to provide such a stethoscope holder which may be easily adhered to clothing.

These and other objects will become apparent to those skilled in the art in light of the following disclosure and accompanying drawings.

In accordance with the invention generally stated, a stethoscope holder is provided which may be secured to a piece of apparel, such as a pocket of a lab coat or the waist band of a pair of pants. The stethoscope holder includes a base having a front surface and a back surface. A rib extends out from the front surface of the base. The rib is generally U-shaped in front elevation having a pair of side sections joined by a curved section and is generally L-shaped in cross-section. The rib thus defines a generally U-shaped channel which removably receives either the bell or diaphragm section of the chestpiece. A notch is formed at a bottom of the curved section of the rib and is sized to accept the tubing of the stethoscope.

A flexible finger extends from the front surface, below the rib and offset from the center of the base to hold at least one of the ear pieces of the stethoscope. The finger has a portion extending from the base which is generally perpendicular to the base, and a second portion extending upwardly from the first portion to be generally parallel to the base. The first and second portions of the finger are joined by a knuckle which has an arcuate inner surface. The finger may be provided with a tab on its inner surface near a top of the second potion. The finger is spaced from the knuckle a distance at least equal to the diameter of the ear piece tubing to actively hold the ear piece to the base.

A spring biased clip is hingedly mounted to the back surface of the base, near the top thereof and is operable to selectively and removably secure the holder to an item of apparel.

BRIEF DESCRIPTION OF THE FIGURES

FIG. 1 is a front elevational view of a stethoscope holder of the present invention with a stethoscope mounted therein;

FIG. 2 is a from elevation view of the stethoscope holder;

FIG. 3 is a side elevational view of the stethoscope holder; and

FIG. 4 is a top plan view of the stethoscope holder.

DESCRIPTION OF THE PREFERRED EMBODIMENT

In FIG. 1, a stethoscope holder 1 of the present invention is shown carrying a stethoscope 3. As is known, a stethoscope includes two ear pieces 5 which are typically made of metal tubing and have plastic endpieces which are sized to fit in the ears of the user. The metal tubing 5 is secured to a pliable rubber tubing 7 by a yoke 9. A chestpiece 11 of the stethoscope 3 is connected to the end of the rubber tubing 7. As is typical, the chestpiece 11 includes a diaphragm section 13 and a bell section 15 spaced apart by a hollow connecting tube (not shown). A connector 17 extends from amplifier tube to connect the chestpiece 11 to the rubber tubing 7.

Turning to FIGS. 2–4, the holder 1 includes a base 21 having a front surface 23 and a back surface 25. The base 21 is shown to be generally rectangular with rounded off bottom corners, but could be made in any desired shape. A generally U-shaped rib 27 extends from the base front surface 23 and includes two side parts 29 which are generally parallel to a longitudinal axis of the base 21 which are joined by a curved section 31. The side parts preferably have a length greater than the largest diameter of the chestpiece 11, and the curved section has a curvature complimentary to the curvature of the chestpiece. In cross-section (or in top plan, as seen in FIG. 4), the rib is generally L-shaped and includes a leg 33 which extends from the base 21 and an inwardly extending finger 35 which is generally perpendicular to the leg and parallel to the base 21. The leg 33 and finger 35 define a generally U-shaped groove 39 which is sized to receive the diaphragm section 13 of the stethoscope chestpiece 11, as seen in FIG. 1. Although sized to receive the chestpiece diaphragm section, the rib 27 could be sized and shaped to receive the bell section 15 of the chestpiece 11. As can be appreciated, the chestpiece simply slides into the groove 39 formed by the rib 27 and is prevented from falling forwardly out of the holder 1 by the rib. The rib 27 thus securely holds the chestpiece 11. To provide a space for the rubber tubing 7, the rib 27 may be provided with a notch 41 sized to receive the tubing 7.

A finger 45 extends from the base surface 23 below the rib 27. The finger 45 is spaced horizontally from the notch 41 such that the finger 45 is not centered between the two sides of the base 21. The finger is bent, and includes a first portion 47 which extends generally perpendicularly from the base 21 and a second portion 49 which extends upwardly from the first portion 47 (with reference to FIGS. 2 and 3) and generally parallel to the base 21. A small tab or protrusion 51 may be formed on the inner surface of the finger second portion near the top thereof. The first and second portions of the finger 45 are joined by a curved knuckle 53 which, at least on the inner surface of the finger, provides a smooth transition between the first and second portions. Stated differently, the inner surface of the knuckle is arcuate. As seen in FIG. 1, the finger 45 is sized and shaped to accept the ear piece tubing 5 of the stethoscope when in a crossed position. The finger 45 is of a thickness which allows the finger to be flexible, to facilitate insertion and removal of the stethoscope ear piece tubing 5 from the finger. The flexibility of the finger 45, along with the tab 51, also helps maintain the ear pieces 5 in the finger 45 when inserted therein. The first portion 47 of the finger 45 is at least slightly larger than the diameter of the ear piece tubing 5, so that the earpiece tubing can fit in the finger, as seen in FIG. 1. Preferably, the finger is sized so that both earpiece tubes can be placed in the finger. If both earpiece tubes are placed in the finger, as seen in FIG. 1, the earpiece tubes will cross each other. Thus, the finger first portion has a length at least slightly greater then twice the diameter of the ear piece tubing 5. The finger second portion 49 also has a length that is greater than the combined diameters of the two ear piece tubings. This will prevent the earpiece tubes 5 from falling out of the finger 45. If the tab or button 51 is provided, the button 51 is spaced from the finger first portion 47 such that one of the, and preferably both of the, earpiece tubings 5 can be received in the finger beneath the button 51.

As can be seen in FIG. 1, the finger is sized to hold both earpiece tubes 5 in a crossing relationship. To place the earpiece tubes in the finger, the ear pieces are crossed over each other, such that the earpiece tubes 5 define an closed arc with the yoke 9, as is shown in FIG. 1. The earpiece tubes are then inserted into the crook of the finger, such that the finger is positioned inside of the cross-over point of the ear pieces.

The stethoscope holder 1 may be secured to a piece of clothing, such as a breast pocket of a lab coat or the waist of a pair of pants, for example. The holder 1 includes a spring operated clip 55 mounted to the back surface 25 of the base 21. The clip 55 is generally standard and includes a pair of spaced apart generally triangularly shaped brackets 57 extending from the back surface 25 of the base 21. The clip 55 includes a clip body 59 having an inner surface 61. A pair spaced apart of triangularly shaped brackets 63 extend from the inner surface 61 near the top thereof. The brackets 63 are spaced apart slightly less than the brackets 57, such that the brackets 63 are positioned adjacent inner surfaces of the brackets 57. An axle 65 extends through the brackets 57 and 63 to pivotally secure the clip body 59 to the holder base 21. The axle 65 thus defines a pivot point for the clip body 59. A pair of springs 67 are mounted on the axle to bias the clip to a closed position. The clip body is bent at the brackets 63 to define a top or finger portion 69 and a lower portion 71. The finger portion 69 of the clip body 59 comprises only a small portion of the clip body and is angled relative to the lower portion to extend generally away from the holder base 21, as seen in FIG. 3. A finger 73 extends inwardly toward the holder base 21 from the bottom of the lower portion 71. When the finger portion 69 is pulled toward the holder body 21, the clip body lower portion 71 and the finger 73 pivot away from the holder body 21 to provide a space between the finger 73 and the holder body 21. The clip may then be applied to a piece of clothing, and, when the top portion is released, the clip will spring back such that the clothing is held between the clip body 59 and the holder body 21.

As can be seen, the foregoing holder is simple to use and will conveniently hold a stethoscope to the waist band of a pair of pants or to the breast pocket of a shirt or lab coat, for example. This description is set forth for illustrative purposes only. Variations within the scope of the appended claims may be apparent to those skilled in the art. For example, the holder may be provided with two fingers 45, each of which will hold one of the ear pieces 5 of the stethoscope. Although the base is shown to be generally flat of planar, it could be curved or arched if desired. The clip 55 could be replaced with a simple hook which could be molded to the base 21. These examples are merely illustrative.

We claim:

1. A stethoscope holder for holding a stethoscope, the stethoscope including a pair of ear pieces mounted to a rubber tubing at one end of the tubing and a chestpiece mounted to another end of the tubing, the chestpiece having a generally circular bell and a generally circular diaphragm; the stethoscope holder including:

a base having a front surface and a back surface;

a rib on the front surface of the base, said rib being generally U-shaped in front elevation; the rib including a pair of side sections joined by a curved section; said rib being generally L-shaped in cross-section, said rib defining a generally U-shaped channel which removably receives said chestpiece, said channel being sized to accept one of said chestpiece bell and diaphragm; and a finger on said front surface of the base adapted to hold at least one of said ear pieces of said stethoscope, said finger having a portion generally perpendicular to the base and a second portion extending upwardly from said first portion generally parallel to the base.

2. The stethoscope holder of claim 1 wherein said finger first and second portions are joined by a knuckle, said knuckle having an arcuate inner surface.

3. The stethoscope holder of claim 2 wherein said finger is flexible.

4. The stethoscope holder of claim 3 wherein said finger includes a tab on said inner surface near a top of said second portion, said tab being spaced from said finger first portion a distance sufficient that at least one of said ear pieces can be received in said finger beneath said tab.

5. The stethoscope holder of claim 1 including a notch formed at a bottom of said curved section of said rib, said notch being sized to accept said tubing of said stethoscope.

6. The stethoscope holder of claim 1 including a spring biased clip hingedly mounted to said back surface of said base, near a top of said base, said clip being operable to selectively and removably secure said holder to an item of apparel.

7. The stethoscope holder of claim 1 wherein said side portions of said rib have a length greater than a diameter of said chestpiece.

8. The stethoscope holder of claim 7 wherein said curved portion of said rib has a curvature complimentary to a curvature of said chestpiece.

9. A stethoscope holder for holding a stethoscope on a piece of apparel, the stethoscope including a pair of ear pieces mounted to a rubber tubing at one end of the tubing and a chestpiece mounted to another end of the tubing, the chestpiece having a generally circular bell and a generally circular diaphragm; the stethoscope holder including:

a base having a front surface and a back surface;

a rib on the front surface of the base, said rib being generally U-shaped in front elevation and L-shaped in cross-section to define a generally U-shaped channel sized to removably receive one of said chestpiece bell and diaphragm of said chestpiece, a resilient finger on said front surface of the base adapted to hold at least one of said ear pieces of said stethoscope, the finger having a free end spaced from the base to define a gap between the finger free end and the base;

and means for mounting said stethoscope holder on a piece of apparel.

10. The stethoscope holder of claim 9 wherein said finger has a first portion extending from said base generally perpendicular to the base and a second portion extending upwardly from said first portion generally parallel to the base, said first and second portions having a length at least equal to the a diameter of the stethoscope earpiece tubing.

11. The stethoscope holder of claim 10 wherein said finger removably receives both ear piece tubings of the stethoscope, said finger first and second portions each having a length at least equal to the combined diameters of the two ear piece tubings.

12. The stethoscope holder of claim 9 wherein said means for attaching the holder to an item of apparel comprises a spring biased clip.

13. The stethoscope holder of claim 9 wherein said finger includes a tab on an inner surface of said finger near said free end.

* * * * *